US012673167B2

(12) United States Patent
Ogino et al.

(10) Patent No.: US 12,673,167 B2
(45) Date of Patent: Jul. 7, 2026

(54) PRE-FILLED SYRINGE

(71) Applicant: NIPRO CORPORATION, Osaka (JP)

(72) Inventors: Ryo Ogino, Osaka (JP); Mitsuru Hasegawa, Osaka (JP)

(73) Assignee: NIPRO CORPORATION, Osaka (JP)

( * ) Notice: Subject to any disclaimer, the term of this patent is extended or adjusted under 35 U.S.C. 154(b) by 616 days.

(21) Appl. No.: 18/025,716

(22) PCT Filed: Sep. 10, 2021

(86) PCT No.: PCT/JP2021/033290
§ 371 (c)(1),
(2) Date: Mar. 10, 2023

(87) PCT Pub. No.: WO2022/054903
PCT Pub. Date: Mar. 17, 2022

(65) Prior Publication Data
US 2023/0364345 A1     Nov. 16, 2023

(30) Foreign Application Priority Data
Sep. 11, 2020     (JP) ................................. 2020-152936

(51) Int. Cl.
*A61M 5/315*     (2006.01)
*A61M 5/19*     (2006.01)
*A61M 5/31*     (2006.01)

(52) U.S. Cl.
CPC .......... *A61M 5/31511* (2013.01); *A61M 5/19* (2013.01); *A61M 2005/3132* (2013.01)

(58) Field of Classification Search
CPC ................ A61M 5/31511; A61M 5/19; A61M 2005/3132
See application file for complete search history.

(56) References Cited

U.S. PATENT DOCUMENTS 4,693,706 A     9/1987   Ennis, III
5,688,252 A     11/1997  Matsuda et al.
(Continued)

FOREIGN PATENT DOCUMENTS

JP     8-150208 A     6/1996
JP     2603027 Y2     2/2000
(Continued)

OTHER PUBLICATIONS

International Search Report for PCT/JP2021/033290 dated Nov. 9, 2021.

*Primary Examiner* — Bradley J Osinski
(74) *Attorney, Agent, or Firm* — Sughrue Mion, PLLC

(57) ABSTRACT

A pre-filled syringe includes a tubular container, a front end gasket, a rear end gasket, an intermediate gasket, and a plunger. The tubular container has an inner peripheral surface, a protruding inner side surface, and a receiving surface. A groove is formed in an outer peripheral surface of the intermediate gasket. The plunger has a connection portion, a pushing portion, and a guide rib. The protruding inner side surface is formed at a position facing the pushing portion in a pushing completion state. The guide rib is provided with a recess. A rear end portion of the recess is located rearward with respect to a rear end portion of the protruding inner side surface in the pushing completion state.

2 Claims, 7 Drawing Sheets

(56)     References Cited

U.S. PATENT DOCUMENTS

| 5,891,087 A | * | 4/1999 | Ohtani | ................. | A61M 5/284 |
| | | | | | 604/218 |
| 2008/0234632 A1 | * | 9/2008 | Hasegawa | ......... | A61M 5/31596 |
| | | | | | 604/218 |
| 2012/0095394 A1 | * | 4/2012 | Kakiuchi | ............. | A61M 5/284 |
| | | | | | 604/89 |
| 2017/0000954 A1 | | 1/2017 | Hasegawa et al. | | |

FOREIGN PATENT DOCUMENTS

| JP | 2004-049726 A | 2/2004 |
| WO | 2005/089837 A1 | 9/2005 |
| WO | 2015/079874 A1 | 6/2015 |

* cited by examiner

FIG.2

PRE-FILLED SYRINGE

TECHNICAL FIELD

The present invention relates to a pre-filled syringe.

BACKGROUND ART

Conventionally, there has been known a pre-filled syringe in which a medicine and a liquid medicine can be mixed with each other in a container. For example, WO 2015/079874 discloses a pre-filled syringe including a tubular container, a front-end side gasket, a rear-end side gasket, an intermediate gasket, and a plunger. Each gasket is slidable in the tubular container. A medicine is accommodated in a front chamber formed between the front-end side gasket and the intermediate gasket in the tubular container, and a liquid agent is accommodated in a rear chamber formed between the rear-end side gasket and the intermediate gasket in the tubular container. The plunger is connected to the rear-end side gasket and can push the rear-end side gasket toward the front end side. The tubular container has a bypass portion provided to protrude outward in the radial direction. A groove communicating the front chamber and the rear chamber with each other is formed in an outer peripheral surface of the intermediate gasket at a position at which the intermediate gasket faces the bypass portion.

In a state in which the plunger is not pushed, the intermediate gasket is located on the rear end side with respect to the bypass portion, and the front chamber and the rear chamber are partitioned by the intermediate gasket. When the plunger is pushed to cause the intermediate gasket to face the bypass portion, the front chamber and the rear chamber communicate with each other, with the result that the liquid agent is pushed by the rear-end side gasket and is accordingly moved toward the front chamber via the groove portion of the intermediate gasket. Thus, the medicine and the liquid agent are mixed with each other. When the plunger is further pushed from this state, the front-end side gasket is pushed until the front end of the front-end side gasket is brought into contact with the bottom surface of the nozzle portion, and when the plunger is further pushed, the mixed liquid of the medicine and the liquid agent is discharged through a clearance between the front end gasket and the nozzle portion.

CITATION LIST

Patent Literature

PTL 1: WO 2015/079874

SUMMARY OF INVENTION

Technical Problem

In the pre-filled syringe described in WO 2015/079874, when the rear end portion of the rear-end side gasket is set to a position facing the bypass portion in a state in which the pushing of the plunger into the tubular container is completed (state in which the front-end side gasket is in contact with the bottom surface of the nozzle portion, the intermediate gasket is in contact with the front-end gasket, and the rear-end side gasket is in contact with the intermediate gasket), the liquid agent or the mixed liquid remaining in the bypass portion may be leaked to the rear end side of the tubular container through a clearance between the tubular container and the plunger due to a capillary phenomenon.

An object of the present invention is to provide a pre-filled syringe to suppress leakage of liquid through a clearance between a tubular container and a plunger in a state in which pushing of the plunger into the tubular container is completed.

Solution to Problem

A pre-filled syringe according to one aspect of the present invention includes: a tubular container capable of accommodating a liquid medicine and a medicine, the tubular container being formed to have a tubular shape, a front end gasket provided in the tubular container, the front end gasket being slidable with respect to the tubular container along an axial direction of the tubular container; a rear end gasket provided rearward with respect to the front end gasket in the tubular container so as to define a space in the tubular container together with the front end gasket, the rear end gasket being slidable with respect to the tubular container along the axial direction of the tubular container; an intermediate gasket provided between the front end gasket and the rear end gasket in the tubular container so as to partition the space into a front chamber adjacent to the front end gasket and a rear chamber adjacent to the rear end gasket, the intermediate gasket being slidable with respect to the tubular container along the axial direction of the tubular container; and a plunger connected to the rear end gasket, the plunger being capable of pushing the rear end gasket toward a front end side of the tubular container along the axial direction, wherein the tubular container has an inner peripheral surface in contact with an outer peripheral surface of the front end gasket, an outer peripheral surface of the intermediate gasket, and an outer peripheral surface of the rear end gasket, a protruding inner side surface having a shape that protrudes from the inner peripheral surface in a direction orthogonal to the axial direction and that extends along the axial direction, and a receiving surface that receives the front end gasket in the axial direction, a groove communicating the front chamber and the rear chamber with each other is formed in the outer peripheral surface of the intermediate gasket at a position at which the intermediate gasket faces the protruding inner side surface, the plunger has a connection portion connected to the rear end gasket, a pushing portion that pushes the rear end gasket, and a guide rib that guides movement of the pushing portion along the axial direction, the guide rib being formed to have a flat plate shape that extends from the pushing portion along the axial direction of the tubular container and that is along a plane including a center axis of the tubular container, the protruding inner side surface is formed at a position facing the pushing portion in a pushing completion state in which the plunger is pushed into the tubular container until the front end gasket is brought into contact with the receiving surface, the intermediate gasket is brought into contact with the front end gasket, and the rear end gasket is brought into contact with the intermediate gasket, the guide rib is provided with a recess having a shape depressed toward the center axis so as to be separated from the inner peripheral surface of the tubular container, and a rear end portion of the recess in the axial direction is located rearward with respect to a rear end portion of the protruding inner side surface in the axial direction in the pushing completion state.

Advantageous Effects of Invention

According to the present invention, there can be provided a pre-filled syringe to suppress leakage of liquid through a clearance between a tubular container and a plunger in a state in which pushing of the plunger into the tubular container is completed.

BRIEF DESCRIPTION OF DRAWINGS

FIG. 2 is a cross sectional view of the pre-filled syringe.

DESCRIPTION OF EMBODIMENTS

Embodiments of the present invention will be described with reference to figures. It should be noted that in the figures referred to below, the same of corresponding members are denoted by the same numerals.

Figure 1:
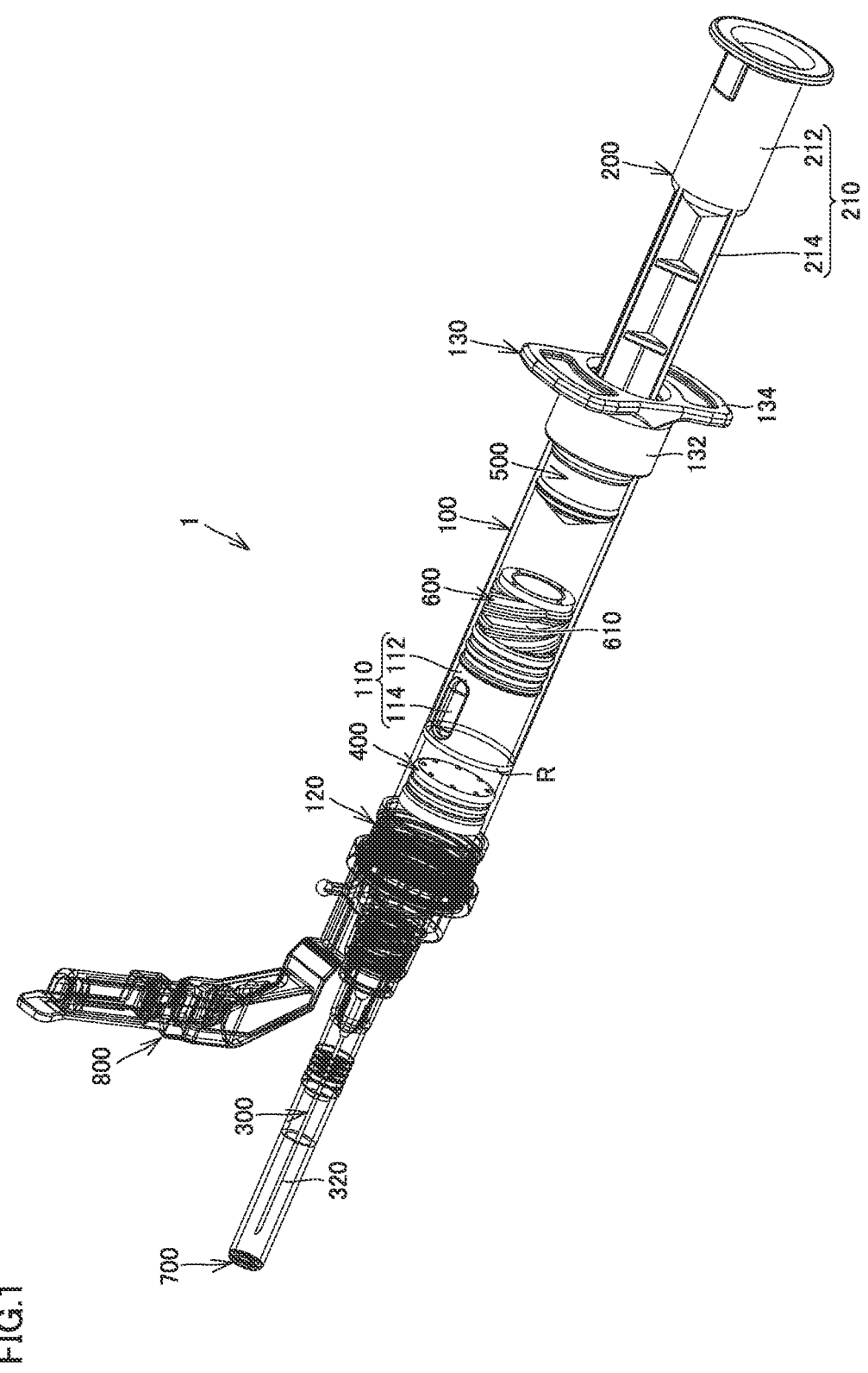
FIG. 1 is a perspective view of a pre-filled syringe according to one embodiment of the present invention.
Figure 2:
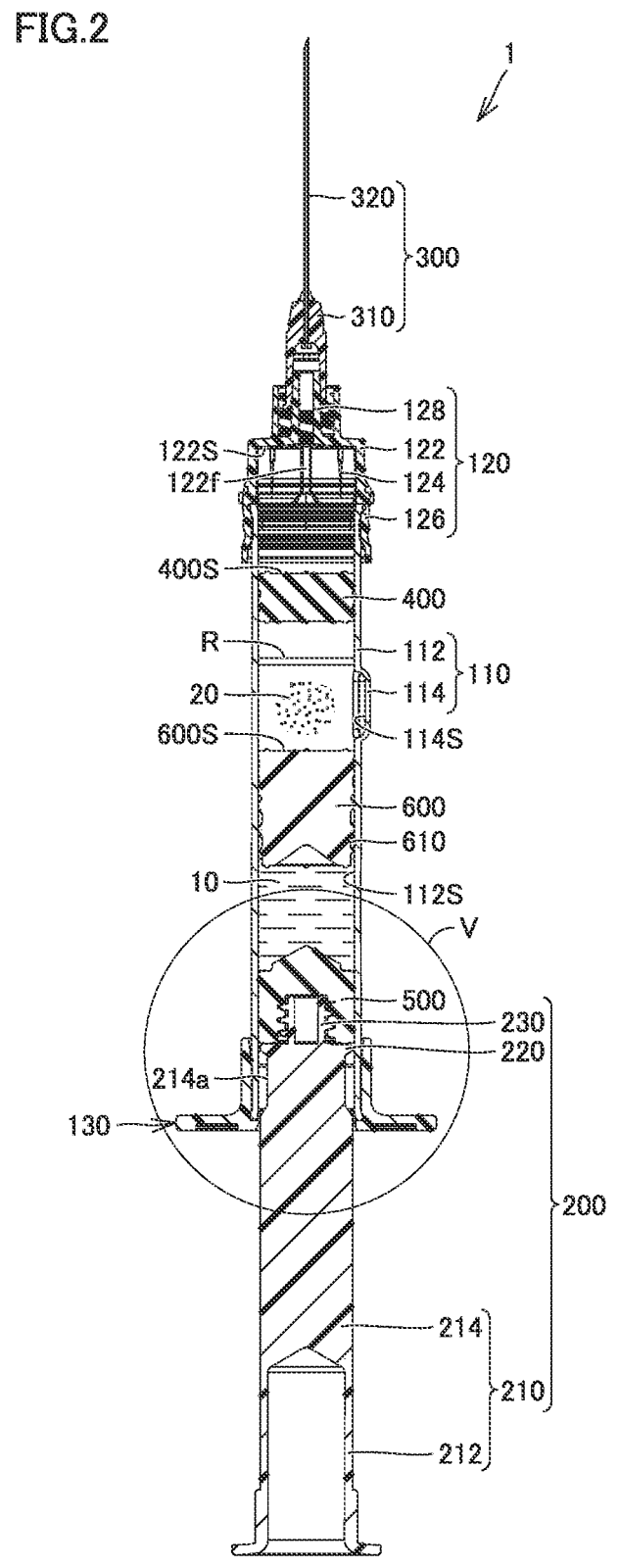

FIG. 1 is a perspective view of a pre-filled syringe according to one embodiment of the present invention FIG. 2 is a cross sectional view of the pre-filled syringe. This pre-filled syringe 1 has a function as a container for a liquid medicine 10 and a medicine 20, and has a function as a syringe. As shown in FIGS. 1 and 2, pre-filled syringe 1 includes liquid medicine 10, medicine 20, a tubular container 100, a plunger 200, an injection needle unit 300, a front end gasket 400, a rear end gasket 500, an intermediate gasket 600, and a cap 700. It should be noted that each of FIGS. 1 and 2 shows pre-filled syringe 1 in a state before use.

Tubular container 100 accommodates liquid medicine 10 and medicine 20 with liquid medicine 10 and medicine 20 being separated from each other. That is, tubular container 100 has a function as a container for liquid medicine 10 and medicine 20. Tubular container 100 has a barrel 110, a nozzle portion 120, and a flange portion 130.

Barrel 110 accommodates liquid medicine 10 and medicine 20. As shown in FIG. 2, a front end portion (end portion on the upper side in FIG. 2) and a rear end portion (end portion on the lower side in FIG. 5) of barrel 110 are opened. Barrel 110 has a barrel main body 112 and a protrusion 114.

Barrel main body 112 is formed to have a cylindrical shape. Barrel main body 112 is provided with a stop ring R. Stop ring R indicates a reference for an amount of pushing of plunger 200 into tubular container 100.

Protrusion 114 has a shape that bulges from barrel main body 112 outward in a radial direction of barrel main body 112 and that extends along an axial direction (upward/downward direction in FIG. 2) of barrel main body 112. An inner side surface of protrusion 114 constitutes a protruding inner side surface 114S (see FIG. 2). Protruding inner side surface 114S has a shape that protrudes from an inner peripheral surface 112S of barrel main body 112 in a direction orthogonal to the axial direction and that extends along the axial direction.

Nozzle portion 120 is connected to the front end portion of barrel main body 112. Nozzle portion 120 has an accommodation portion 122, ribs 124, an attachment portion 126, and a discharge portion 128.

Accommodation portion 122 can accommodate front end gasket 400. Accommodation portion 122 is located on the front end side with respect to barrel main body 112. An inner surface of accommodation portion 122 is provided with a flow path 122f for discharging a mixed liquid of liquid medicine 10 and medicine 20. This flow path 122f has a shape depressed from other regions of the inner surface of accommodation portion 122 than flow path 122f. Accommodation portion 122 has a receiving surface 122S that receives front end gasket 400 in the axial direction. As shown in FIG. 1, a protective member 800 is attached to accommodation portion 122.

Each of ribs 124 is provided on the inner peripheral surface of accommodation portion 122 at a region different from flow path 122f. Rib 124 has a shape that protrudes inward in the radial direction from the inner peripheral surface of accommodation portion 122 and that extends along the axial direction. Ribs 124 are provided at equal intervals along the peripheral direction of accommodation portion 122.

Attachment portion 126 is a region that is attached to the front end portion of barrel main body 112. Attachment portion 126 has a shape extending rearward from a rear end portion of accommodation portion 122. Attachment portion 126 is formed to have a cylindrical shape.

Discharge portion 128 has a shape extending frontward from the front end of accommodation portion 122. The inside of discharge portion 128 is connected to flow path 122f.

Injection needle unit 300 is connected to discharge portion 128. Injection needle unit 300 has: a base body 310 connected to discharge portion 128; and a piercing needle 320 held by base body 310. Before pre-filled syringe 1 is used as a syringe, piercing needle 320 is covered with cap 700 (see FIG. 1).

Flange portion 130 is connected to a rear end portion of barrel main body 112. Flange portion 130 has an attachment tubular portion 132, a projection 134, and an abutment portion 136.

Attachment tubular portion 132 is a region that is attached to the rear end portion of barrel main body 112. Attachment tubular portion 132 is formed to have a cylindrical shape.

Projection 134 has a shape projecting outward from the rear end portion of attachment tubular portion 132 in the radial direction.

Abutment portion 136 is connected to an end portion of projection 134 on the inner side in the radial direction.

Figure 6:
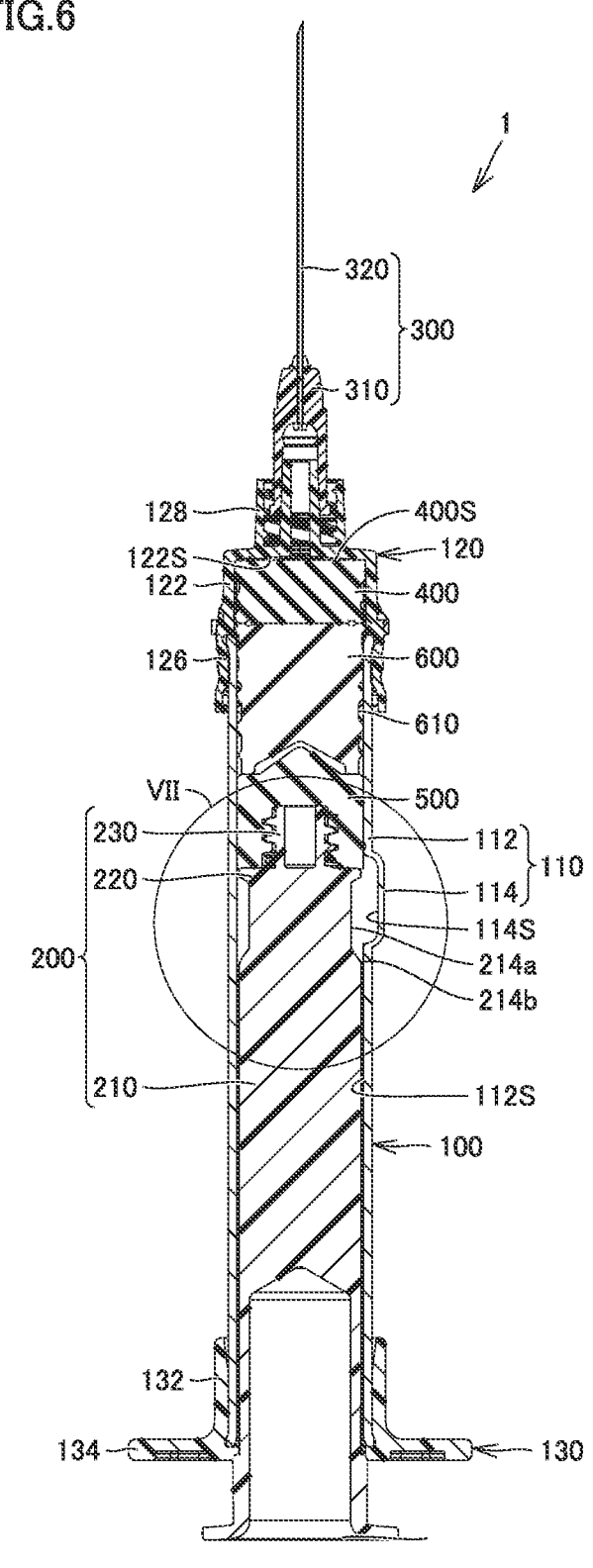
FIG. 6 is a cross sectional view in a pushing completion state.

Front end gasket 400 is provided in tubular container 100. Specifically, front end gasket 400 is accommodated in barrel main body 112 on the front end side with respect to protrusion 114 before the use of pre-filled syringe 1. Front end gasket 400 is in close contact with inner peripheral surface 112S of barrel main body 112. Front end gasket 400 is slidable with respect to barrel main body 112 and accommodation portion 122 along the axial direction. As shown in FIG. 6, in a state in which front end surface 400S of front end gasket 400 is in contact with receiving surface 122S of accommodation portion 122, front end gasket 400 is separated from barrel main body 112. In this state, the mixed liquid is discharged through flow path 122f.

Figure 5:
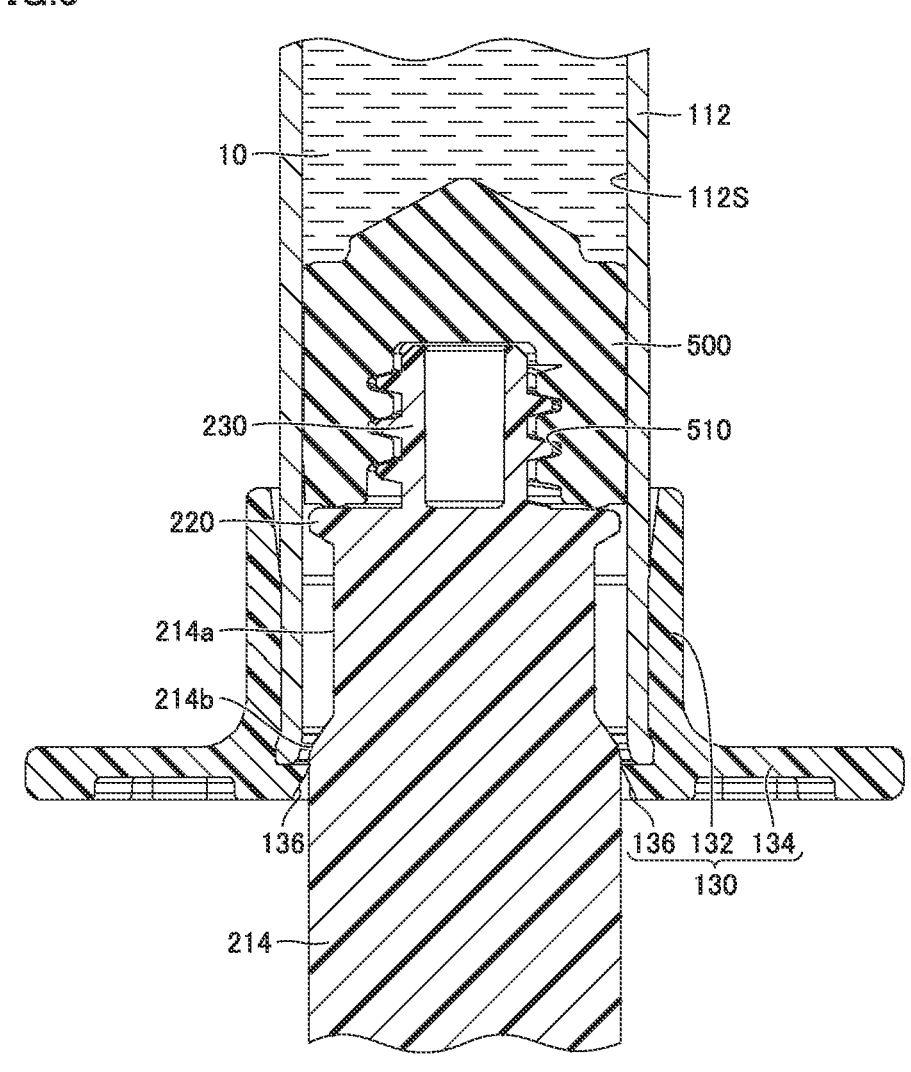
FIG. 5 is an enlarged view of a range indicated by a solid line V in FIG. 2.

Rear end gasket 500 is provided rearward with respect to front end gasket 400 in tubular container 100 so as to define a space in tubular container 100 together with front end gasket 400. Rear end gasket 500 is in close contact with inner peripheral surface 112S of barrel main body 112. Rear end gasket 500 is slidable with respect to barrel main body 112 along the axial direction. As shown in FIG. 5, a female thread portion 510 is formed in rear end gasket 500.

Intermediate gasket 600 is provided between front end gasket 400 and rear end gasket 500 in barrel main body 112 of tubular container 100 so as to partition the space into a front chamber and a rear chamber. As shown in FIG. 2, intermediate gasket 600 is accommodated in barrel main body 112 on the rear end side with respect to protrusion 114 before the use of pre-filled syringe 1.

The front chamber is a space adjacent to front end gasket 400. More specifically, the front chamber is a space defined by front end gasket 400, intermediate gasket 600, and barrel 110. Medicine 20 is accommodated in the front chamber.

The rear chamber is a space adjacent to rear end gasket 500. More specifically, the rear chamber is a space defined by rear end gasket 500, intermediate gasket 600, and barrel 110. Liquid medicine 10 is accommodated in the rear chamber.

Intermediate gasket 600 is in close contact with inner peripheral surface 112S of barrel main body 112. Intermediate gasket 600 is slidable with respect to barrel main body 112 along the axial direction. A groove 610 communicating the front chamber and the rear chamber with each other is formed in the outer peripheral surface of intermediate gasket 600 at a position at which intermediate gasket 600 faces protruding inner side surface 114S.

Figure 3:
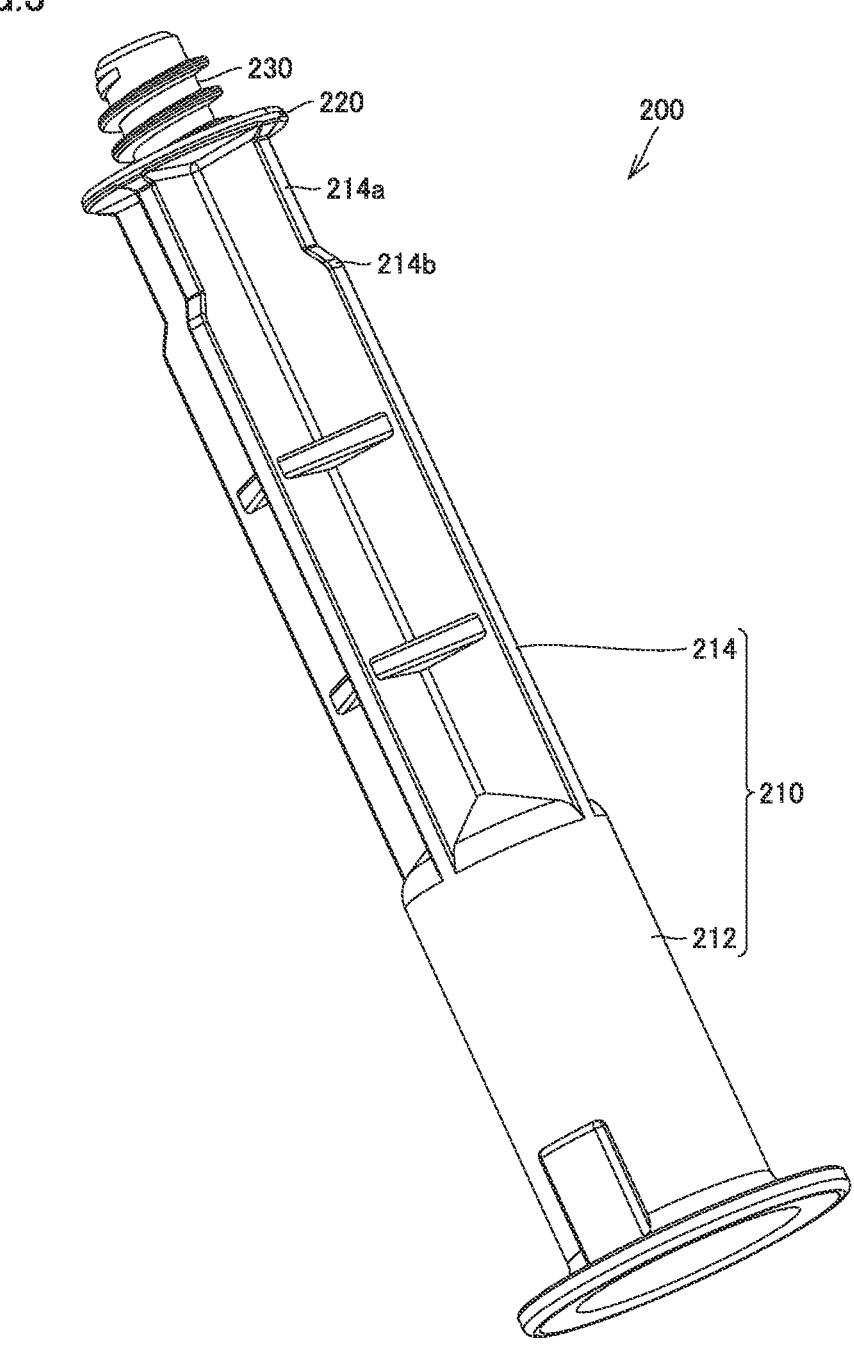
FIG. 3 is a perspective view of a plunger.
Figure 4:
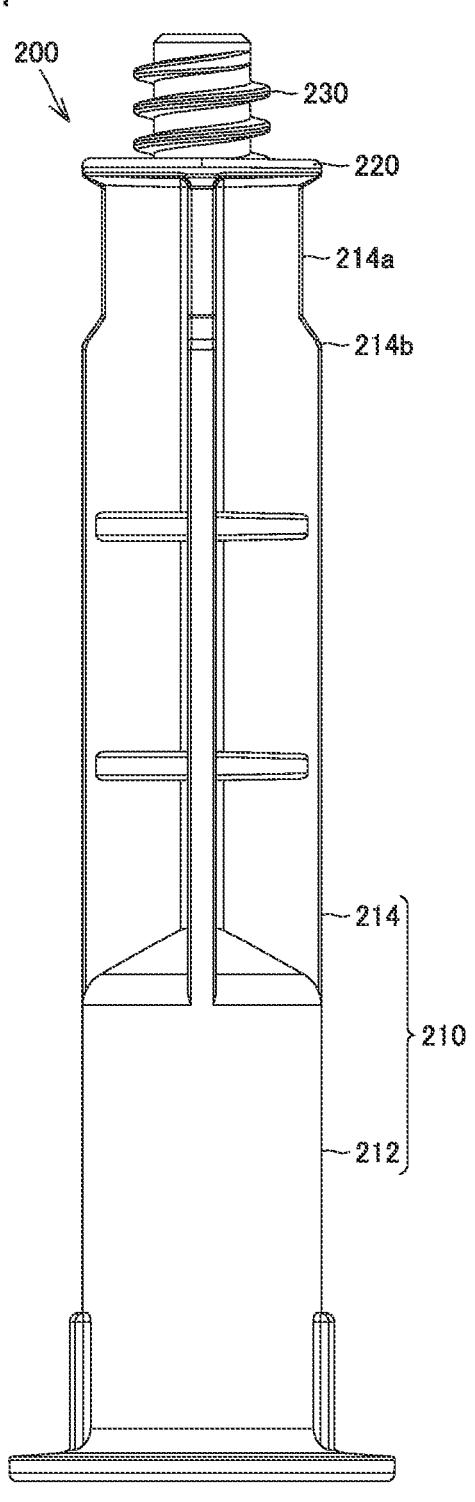
FIG. 4 is a front view of the plunger.

Plunger 200 is connected to rear end gasket 500. Plunger 200 can push rear end gasket 500 toward the front end side of tubular container 100 along the axial direction. As shown in FIGS. 3 and 4, plunger 200 has a stem portion 210, a pushing portion 220, and a connection portion 230.

Connection portion 230 is connected to rear end gasket 500. Connection portion 230 has a male thread portion screwed into female thread portion 510 of rear end gasket 500.

Pushing portion 220 is connected to a rear end portion of connection portion 230. Pushing portion 220 pushes rear end gasket 500. Pushing portion 220 is formed to have a circular plate shape.

Figure 7:
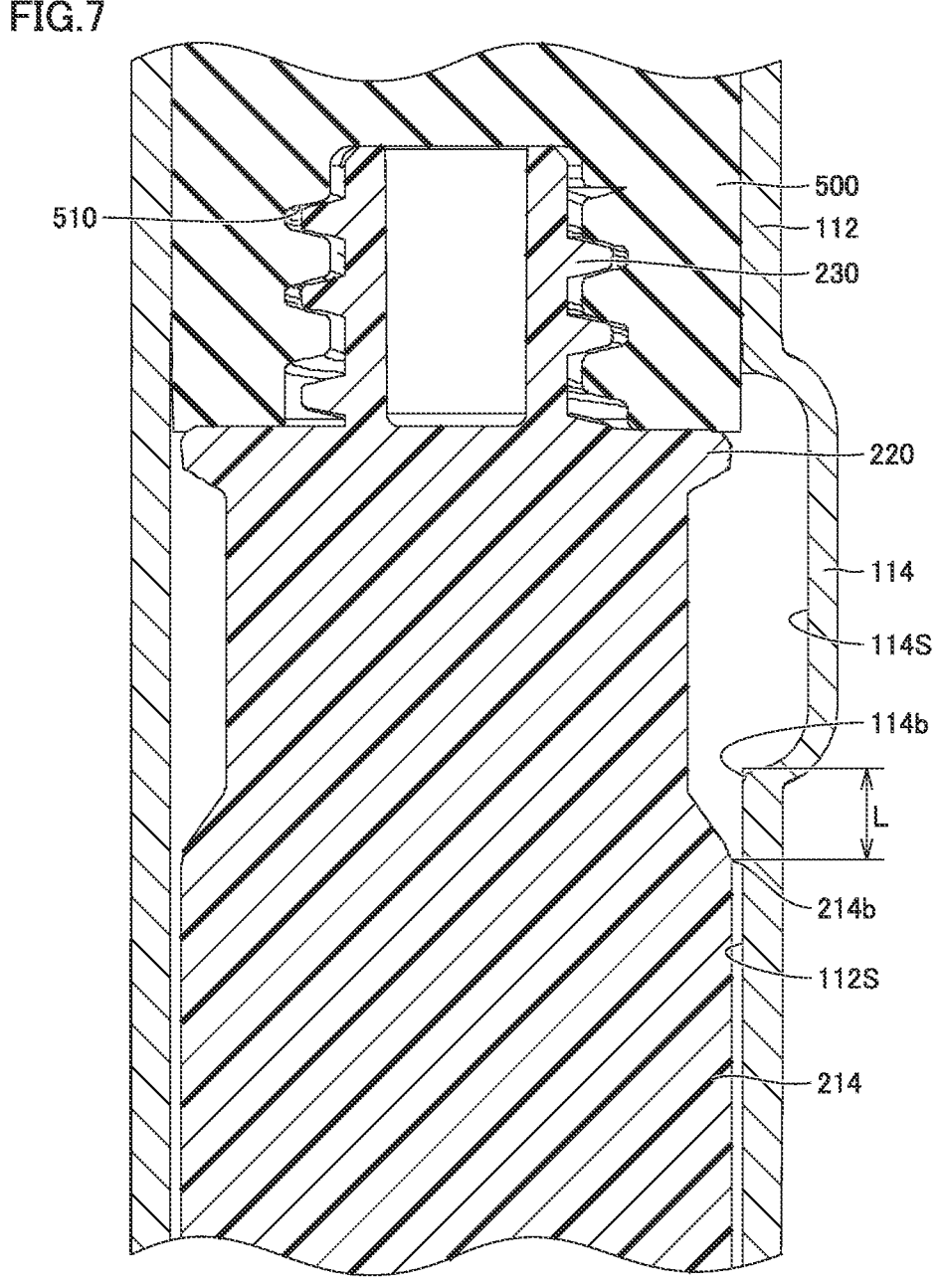
FIG. 7 is an enlarged view of a range indicated by a solid line VII in FIG. 6.

FIG. 6 is a cross sectional view in a pushing completion state (state in which plunger 200 is pushed into tubular container 100 until front end gasket 400 is brought into contact with receiving surface 122S, intermediate gasket 600 is brought into contact with front end gasket 400, and rear end gasket 500 is brought into contact with intermediate gasket 600). FIG. 7 is an enlarged view of a range indicated by a solid line VII in FIG. 6.

As shown in FIGS. 6 and 7, pushing portion 220 faces protruding inner side surface 114S in the pushing completion state. In other words, protruding inner side surface 114S is formed at a position facing pushing portion 220 in the pushing completion state.

Stem portion 210 has a shape extending rearward from the rear end surface of pushing portion 220 along the axial direction of barrel 110. Stem portion 210 has a cylindrical portion 212 and guide ribs 214.

Each of guide ribs 214 guides movement of pushing portion 220 with respect to barrel 110 along the axial direction. Guide rib 214 is formed to have a flat plate shape that extends rearward from pushing portion 220 along the axial direction and that is along a plane including the center axis of tubular container 100. In the present embodiment, plunger 200 has four guide ribs 214. Guide ribs 214 are disposed at intervals of 90° around the center axis. Cylindrical portion 212 is connected to a rear end portion of each guide rib 214.

Guide rib 214 is provided with a recess 214a. Recess 214a has a shape depressed toward the center axis so as to be separated from inner peripheral surface 112S of barrel main body 112 of tubular container 100. As shown in FIG. 7, a rear end portion 214b of recess 214a in the axial direction is located rearward with respect to a rear end portion 114b of protruding inner side surface 114S in the axial direction in the pushing completion state. That is, in the pushing completion state, a predetermined distance L is secured between rear end portion 114b of protruding inner side surface 114S and rear end portion 214b of recess 214a.

As shown in FIG. 5, in a state in which plunger 200 is not pushed (state in which pushing portion 220 does not push rear end gasket 500), abutment portion 136 is in abutment with a region of guide rib 214 on the rear end side with respect to recess 214a in the axial direction. Abutment portion 136 is preferably formed to have an annular shape.

Next, a method of using pre-filled syringe 1 will be described.

First, as shown in FIG. 2, the posture of pre-filled syringe 1 is adjusted such that injection needle unit 300 faces upward. In this state, plunger 200 is pushed upward into tubular container 100.

When groove 610 of intermediate gasket 600 faces protruding inner side surface 114S, the front chamber and the rear chamber communicate with each other, with the result that liquid medicine 10 in the rear chamber is pushed by rear end gasket 500 to move toward the front chamber via the clearance between groove 610 of intermediate gasket 600 and protruding inner side surface 114S. Thus, liquid medicine 10 and medicine 20 are mixed with each other. It should be noted that on this occasion plunger 200 is pushed until front end surface 600S of intermediate gasket 600 coincides with stop ring R (see FIGS. 1 and 2). In this state, a portion of front end gasket 400 is located in accommodation portion 122, and front end surface 400S of front end gasket 400 is separated from receiving surface 122S.

In a state in which front end surface 600S of intermediate gasket 600 coincides with stop ring R, tapping or the like is performed, and plunger 200 is thereafter pushed further. Accordingly, front end gasket 400 is separated from barrel main body 112, and front end surface 400S of front end gasket 400 is brought into contact with receiving surface 122S. When plunger 200 is further pushed from this state, the mixed liquid is discharged through flow path 122f and piercing needle 320. Then, when the pushing completion state shown in FIGS. 6 and 7 is attained, the discharging of the mixed liquid is ended.

In this pre-filled syringe 1, part of liquid medicine 10 or the mixed liquid may remain in protrusion 114 or pushing portion 220 in the pushing completion state. However, in pre-filled syringe 1 of the present embodiment, since rear end portion 214b of recess 214a is located rearward with respect to rear end portion 114b of protruding inner side surface 114S in the pushing completion state, distance L from protruding inner side surface 114S to the clearance between the region of guide rib 214 rearward with respect to recess 214a and inner peripheral surface 112S of barrel main body 112 is secured. Accordingly, leakage of liquid through the clearance between tubular container 100 and plunger 200 in the pushing completion state is suppressed

[Implementations]

It will be appreciated by those skilled in the art that the exemplary embodiments described above are specific examples of the following implementations.

A pre-filled syringe according to one aspect of the present disclosure includes: a tubular container capable of accommodating a liquid medicine and a medicine, the tubular container being formed to have a tubular shape; a front end gasket provided in the tubular container, the front end gasket being slidable with respect to the tubular container along an axial direction of the tubular container; a rear end gasket provided rearward with respect to the front end gasket in the tubular container so as to define a space in the tubular container together with the front end gasket, the rear end gasket being slidable with respect to the tubular container along the axial direction of the tubular container: an intermediate gasket provided between the front end gasket and the rear end gasket in the tubular container so as to partition the space into a front chamber adjacent to the front end gasket and a rear chamber adjacent to the rear end gasket, the intermediate gasket being slidable with respect to the tubular container along the axial direction of the tubular container; and a plunger connected to the rear end gasket, the plunger being capable of pushing the rear end gasket toward a front end side of the tubular container along the axial direction, wherein the tubular container has an inner peripheral surface in contact with an outer peripheral surface of the front end gasket, an outer peripheral surface of the intermediate gasket, and an outer peripheral surface of the rear end gasket, a protruding inner side surface having a shape that protrudes from the inner peripheral surface in a direction orthogonal to the axial direction and that extends along the axial direction, and a receiving surface that receives the front end gasket in the axial direction, a groove communicating the front chamber and the rear chamber with each other is formed in the outer peripheral surface of the intermediate gasket at a position at which the intermediate gasket faces the protruding inner side surface, the plunger has a connection portion connected to the rear end gasket, a pushing portion that pushes the rear end gasket, and a guide rib that guides movement of the pushing portion along the axial direction, the guide rib being formed to have a flat plate shape that extends from the pushing portion along the axial direction of the tubular container and that is along a plane including a center axis of the tubular container, the protruding inner side surface is formed at a position facing the pushing portion in a pushing completion state in which the plunger is pushed into the tubular container until the front end gasket is brought into contact with the receiving surface, the intermediate gasket is brought into contact with the front end gasket, and the rear end gasket is brought into contact with the intermediate gasket, the guide rib is provided with a recess having a shape depressed toward the center axis so as to be separated from the inner peripheral surface of the tubular container, and a rear end portion of the recess in the axial direction is located rearward with respect to a rear end portion of the protruding inner side surface in the axial direction in the pushing completion state.

In this pre-filled syringe, since the rear end portion of the recess is located rearward with respect to the rear end portion of the protruding inner side surface in the pushing completion state, the distance from the protruding inner side surface to the clearance between the region of the guide rib rearward with respect to the recess and the tubular container is secured. Accordingly, leakage of liquid through the clearance between the tubular container and the plunger in the pushing completion state is suppressed.

Further, preferably, the tubular container has an abutment portion in abutment with a region of the guide rib on a rear end side with respect to the recess in the axial direction in a state in which the pushing portion does not push the rear end gasket.

In this way, unsteadiness of the plunger with respect to the tubular container in the state in which the pushing portion does not push the rear end gasket is suppressed.

Further, it is preferable to further include a medicine accommodated in the front chamber and a liquid medicine accommodated in the rear chamber.

It should be noted that the embodiments disclosed herein are illustrative and non-restrictive in any respect. The scope of the present invention is defined by the terms of the claims, rather than the description of the embodiments described above, and is intended to include any modifications within the scope and meaning equivalent to the terms of the claims.

REFERENCE SIGNS LIST

1: pre-filled syringe; 10: liquid medicine; 20: medicine; 100: tubular container; 110: barrel; 112: barrel main body; 112S: inner peripheral surface; 114: protrusion; 114S: protruding inner side surface: 114b: rear end portion; 120; nozzle portion; 122: accommodation portion; 122S: receiving surface; 1227 flow path; 124: rib; 126: attachment portion; 128: discharge portion; 130: flange portion, 132: attachment tubular portion; 134: projection; 136; abutment portion; 200: plunger; 210: stem portion, 212: cylindrical portion; 214: guide rib, 214a: recess, 214b: rear end portion; 220: pushing portion; 230; connection portion; 300: injection needle unit; 310; base body: 320: piercing needle: 400: front end gasket; 500; rear end gasket; 510: female thread portion; 600: intermediate gasket; 610: groove; 700: cap; 800; protective member.

The invention claimed is:

1. A pre-filled syringe comprising:
   a tubular container capable of accommodating a liquid medicine and a medicine, the tubular container being formed to have a tubular shape;
   a front end gasket provided in the tubular container, the front end gasket being slidable with respect to the tubular container along an axial direction of the tubular container;
   a rear end gasket provided rearward with respect to the front end gasket in the tubular container so as to define a space in the tubular container together with the front end gasket, the rear end gasket being slidable with respect to the tubular container along the axial direction of the tubular container;
   an intermediate gasket provided between the front end gasket and the rear end gasket in the tubular container so as to partition the space into a front chamber adjacent to the front end gasket and a rear chamber adjacent to the rear end gasket, the intermediate gasket being slidable with respect to the tubular container along the axial direction of the tubular container; and
   a plunger connected to the rear end gasket, the plunger being capable of pushing the rear end gasket toward a front end side of the tubular container along the axial direction, wherein
   the tubular container has
      an inner peripheral surface in contact with an outer peripheral surface of the front end gasket, an outer peripheral surface of the intermediate gasket, and an outer peripheral surface of the rear end gasket,
      a protruding inner side surface having a shape that protrudes from the inner peripheral surface in a direction orthogonal to the axial direction and that extends along the axial direction, and
      a receiving surface that receives the front end gasket in the axial direction,
   a groove communicating the front chamber and the rear chamber with each other is formed in the outer peripheral surface of the intermediate gasket at a position at which the intermediate gasket faces the protruding inner side surface, the plunger has a connection portion connected to the rear end gasket, a pushing portion that pushes the rear end gasket, and a guide rib that guides movement of the pushing portion along the axial direction, the guide rib being formed to have a flat plate shape that extends from the pushing portion along the axial direction of the tubular container and that is along a plane including a center axis of the tubular container, the protruding inner side surface is formed at a position facing the pushing portion in a pushing completion state in which the plunger is pushed into the tubular container until the front end gasket is brought into contact with the receiving surface, the intermediate gasket is brought into contact with the front end gasket, and the rear end gasket is brought into contact with the intermediate gasket, the guide rib is provided with a recess having a shape depressed toward the center axis so as to be separated from the inner peripheral surface of the tubular container, and a rear end portion of the recess in the axial direction is located rearward with respect to a rear end portion of the protruding inner side surface in the axial direction in the pushing completion state, in the pushing completion state, the pushing portion and a front end portion of the recess in the axial direction face the protruding inner side surface, and a rear end portion of the recess in the axial direction is located rearward with respect to a rear end portion of the protruding inner side surface in the axial direction.

2. The pre-filled syringe according to claim 1, wherein the tubular container has an abutment portion in abutment with a region of the guide rib on a rear end side with respect to the recess in the axial direction in a state in which the pushing portion does not push the rear end gasket.

\* \* \* \* \*